United States Patent
Bernhardt et al.

(10) Patent No.: US 8,908,826 B2
(45) Date of Patent: Dec. 9, 2014

(54) METHOD AND SYSTEM UNIT FOR STEREOSCOPIC X-RAY IMAGING

(75) Inventors: Philipp Bernhardt, Forchheim (DE); Martin Spahn, Erlangen (DE)

(73) Assignee: Siemens Aktiengesellschaft, Munich (DE)

(*) Notice: Subject to any disclaimer, the term of this patent is extended or adjusted under 35 U.S.C. 154(b) by 302 days.

(21) Appl. No.: 13/586,073

(22) Filed: Aug. 15, 2012

(65) Prior Publication Data
US 2013/0216021 A1 Aug. 22, 2013

(30) Foreign Application Priority Data
Aug. 25, 2011 (DE) .......................... 10 2011 081 550

(51) Int. Cl.
*A61B 6/02* (2006.01)
*A61B 6/00* (2006.01)
*H01J 35/30* (2006.01)

(52) U.S. Cl.
CPC .............. *A61B 6/022* (2013.01); *A61B 6/4208* (2013.01); *A61B 6/50* (2013.01); *G01N 2223/414* (2013.01); *A61B 6/4007* (2013.01); *A61B 6/545* (2013.01); *A61B 6/4441* (2013.01); *H01J 35/305* (2013.01); *A61B 6/486* (2013.01); *A61B 6/504* (2013.01); *A61B 6/542* (2013.01)
USPC ............................................... 378/42; 378/62

(58) Field of Classification Search
CPC .... A61B 6/022; A61B 6/4007; A61B 6/4441; A61B 6/486
USPC ........... 378/41, 42, 62, 193–197; 250/370.08, 250/370.09, 370.11
See application file for complete search history.

(56) References Cited

U.S. PATENT DOCUMENTS

| | | | |
|---|---|---|---|
| 4,769,701 A | 9/1988 | Hahm | |
| 2009/0238334 A1* | 9/2009 | Brahme et al. | 378/41 |

FOREIGN PATENT DOCUMENTS

| | | |
|---|---|---|
| DE | 3623053 A1 | 1/1988 |
| DE | 112007002364 T5 | 8/2009 |

OTHER PUBLICATIONS

"Stereoskopie": Wikipedia (http://de.wikipedia.org/wiki/Stereoskopie; Stand: Jan. 8, 2011); Others; 2011.

* cited by examiner

*Primary Examiner* — Courtney Thomas

(57) ABSTRACT

A method for stereoscopic x-ray imaging by a stereoscopic x-ray tube and by an x-ray radiation detector is provided. The x-ray radiation detector has a buffer. The stereoscopic x-ray tube has two x-ray beam sources disposed a short distance from one another. 2D image datasets are acquired at relatively short intervals one after the other, which have good quality.

10 Claims, 10 Drawing Sheets

METHOD AND SYSTEM UNIT FOR STEREOSCOPIC X-RAY IMAGING

CROSS REFERENCE TO RELATED APPLICATIONS

This application claims priority of German application No. 10 2011 081 550.3 filed Aug. 25, 2011, which is incorporated by reference herein in its entirety.

FIELD OF INVENTION

The present application relates to a method for stereoscopic x-ray imaging. The present application also relates to a corresponding system unit for stereoscopic x-ray imaging.

BACKGROUND OF INVENTION

X-ray systems are frequently used for imaging for the purposes of diagnostic examination and for interventions, for example in the areas of cardiology, radiology and surgery. These x-ray systems generally comprise a C-arm, on which an x-ray tube and x-ray detector are disposed opposite one another, a patient couch and a system control and display unit. Systems with two planes, i.e. with two C-arms, are also used in interventional radiology.

Monoplane systems, i.e. x-ray systems with one tube and one detector, are used both for diagnostic purposes, e.g. during native vessel display using contrast agents, digital subtraction angiography DSA, and cone-beam computed tomography for generating volumetric datasets, and during interventions such as for example percutaneous transluminal coronary angioplasty PTCA, balloon dilation, coiling, embolization and ablation.

Biplane systems are used when it is necessary to display a vessel or aneurism for example from different angles virtually simultaneously, such as for an intervention, to give a better picture of actual spatial conditions. Fields of application include for example neuroradiology, cardiological electrophysiology and pediatric cardiology.

Displaying an organ from two projection directions using two detector planes, in other words a biplane system, however does not permit the generation of a spatial or 3D impression of different structures of an organ, for example the intersection of vessels or position of an aneurism, or other objects. Any perception of foreground and background is only possible to a limited degree.

One method of obtaining a spatial impression of an object is offered by what is known as stereoscopy. German Wikipedia describes stereoscopy by way of example as follows: "Stereoscopy (Greek stereos=space/spatial, firm/solid–skopeo=to look at) is the reproduction of images with a spatial impression of depth which is physically not present. Stereoscopy is also incorrectly referred to colloquially as "3D", even though it only involves two-dimensional images which convey a spatial impression" and also "The principle is based on the fact that, like all primates and most predators, people look at their surroundings simultaneously from two angles through their two eyes. This allows their brain to assign a distance efficiently to all viewed objects, giving a three-dimensional image of said surroundings, without having to keep moving the head. Stereoscopy simply deals with bringing different two-dimensional images from two slightly differing viewing angles to the left and right eyes. The methods used to do this however vary."

Stereoscopy can also be used in the field of x-ray imaging. One embodiment is described for example in U.S. Pat. No. 4,769,701. Two x-ray focuses are used here, being positioned a certain distance from one another, their central beams intersecting in the recording plane. These generate radiation one after the other and this is registered on an x-ray detector. The images, each of which was recorded from a different perspective, are then supplied separately by a dedicated apparatus to the left and right eye respectively of a viewer. This produces the three-dimensional impression.

When using stereoscopy in medical x-ray imaging there are certain objects that have to be achieved. One object relates to the possible movement of an object or organ. During intervention-related and similarly diagnostic examinations there are for example organs which are non-moving, for example fixed craniums or extremities. Other organs exhibit only slight movement, for example the liver. Others are in constant motion, with sometimes significant amplitudes, for example the heart or aorta. Objects such as catheters, wires or coils, are moved during intervention-related examinations. And finally there is motion caused by a patient moving or a patient couch or the C-arm of the x-ray device being displaced. Possible applications are for example interventional cardioangiography or electrophysiology, e.g. when the endocardium is punctured using a transseptal needle. With moving objects however it should be ensured that imaging takes place virtually simultaneously from the two projection directions, so that a time correlation is ensured between the two projection images. If the differences between the two images are not only due to the different projection settings, but are also due to movement, an identical spatial assignment of the object in the stereo image is not possible. Simultaneous recording of the two images is not possible in principle due to the one x-ray detector, so there is always a certain time interval between the recording of the two images. This means that there is deterioration in image quality for moving objects.

SUMMARY OF INVENTION

The object of the present application is to specify a method and a system unit for stereoscopic x-ray imaging, which offer better image quality, such as for moving objects, than the methods and systems known from the prior art.

The application achieves this object with a method for stereoscopic x-ray imaging having the features of the first independent claim and a system unit for stereoscopic x-ray imaging having the features of the second independent claim.

The basic concept of the application is a method for stereoscopic x-ray imaging with the aid of a stereoscopic x-ray tube, which comprises two x-ray beam sources disposed a short distance from one another, an x-ray radiation detector, which has a scintillator, which converts x-ray beam quanta striking the x-ray radiation detector to light quanta and which also has a grid of detector units, each detector unit having a light-sensitive receiver, at which a measurement value is changed by light quanta striking it, and each detector unit having a buffer for measurement values read out from the light-sensitive receiver, the method comprising the following method steps:

S1) Resetting the measurement values in all the light-sensitive receivers to a predefined value;
S2) Emitting x-ray radiation from the first x-ray beam source, so that said x-ray radiation passes through an image object before striking the x-ray radiation detector;
S3) Reading the measurement values out from all the light-sensitive receivers into the associated buffers and then resetting the measurement values in each receiver to the predefined value;

S4) Emitting x-ray radiation from the second x-ray beam source, so that said x-ray radiation passes through the image object before striking the x-ray radiation detector;
S5) Reading the measurement values out from all the buffers into a central memory, producing a first x-ray image dataset from the projection direction of the first x-ray beam source;
S6) Reading the measurement values out from all the light-sensitive receivers into the central memory, producing a second x-ray image dataset from the projection direction of the second x-ray beam source.

Stereoscopic x-ray imaging takes place with the aid of a stereoscopic x-ray tube, the two x-ray beam sources, i.e. focuses, of which are disposed a short distance from one another. A short distance refers to a distance of approx. 65 mm, the average distance between human eyes, to for example 10 cm to 20 cm or more for an enhanced stereoscopic effect. The distance between the x-ray beam source focuses is also referred to as the stereo base. Stereoscopic x-ray imaging also takes place with the aid of an x-ray radiation detector, which not only has a scintillator and a grid of detector units with light-sensitive receivers, which are embodied as photodiodes for example but also a buffer for measurement values read out from the light-sensitive receiver on each detector unit. The method comprises method steps S1 to S6.

In method step S1 the measurement value is first reset at all the light-sensitive receivers, i.e. the voltage is set to a fixed negative value, known as the bias voltage.

In method step S2 x-ray radiation is then emitted from the first x-ray beam source of the x-ray tube, so that it passes through an image object before striking the x-ray radiation detector. In this process the photodiode is partially or even completely discharged as a function of the incident light.

In method step S3 the measurement value is read out from all the light-sensitive receivers into the associated buffer, i.e. into the buffer of the same detector element. The measurement value is also reset to the negative bias voltage in each light-sensitive receiver.

In method step S4 x-ray radiation is emitted from the second x-ray beam source of the x-ray tube, so that it passes through the image object before striking the x-ray radiation detector.

In method step S5, after or at the same time as method step S4, the measurement value is read out from all the buffers into a central memory, producing a first x-ray image dataset from the projection direction of the first x-ray beam source.

In method step S6 the measurement value is also read out from all the light-sensitive receivers into the central memory, producing a second x-ray image dataset from the projection direction of the second x-ray beam source.

As a result of the application a minimum of time is lost between the recording of two x-ray images, in other words between the acquisition of two x-ray image datasets, with different projections, because the measurement value is not read directly out from the light-sensitive receivers into the central memory in a time-consuming manner but is read out into the buffer in a time-saving manner. As a result the difference between the two x-ray images from slightly offset projections is minimal in the event of possible movement of the image object, so the stereoscopic image is of high quality even under such difficult recording conditions.

In one embodiment of the application in method step S6 the measurement values are first read into the buffer or out from the light-sensitive receivers into the buffer and are then read out from the buffer into the central memory. In this embodiment there is no need for a special read-out mechanism from the light-sensitive receiver to the central memory. Instead it is sufficient to have read-out facilities for reading a measurement value out from the respective light-sensitive receiver into the buffer and at the same time read-out facilities for reading a measurement value out from the buffer into the central memory. This allows the x-ray radiation detector used for the method to have a compact and low-cost structure.

In one development the method steps S1 to S6 are executed repeatedly with a predefinable interval until a termination criterion, such as actuation of a pushbutton, is satisfied. With this embodiment changes over time in an image object can be made visible in a stereoscopic representation, in other words stereoscopic fluoroscopy or staged operation. The predefinable interval here is equal to the inverse of a desired image frequency, the interval being for example 100 ms for an image frequency of 10 Hz, i.e. ten stereoscopic images per second. Image acquisition ends when a termination criterion is satisfied. The termination criterion can be for example pressing a pushbutton, reaching a certain number of images or reaching a time period.

In a further embodiment a peripheral electronic detector unit controls the progress of the method and/or performs an analog/digital conversion of the measurement values and/or prepares the x-ray image datasets, wherein the geometric arrangement is able to be changed, detector-specific corrections are able to be performed or elements of the x-ray image dataset are able to be combined in the process and/or feeds the x-ray image datasets to a system computation unit. The peripheral electronic detector unit can be embodied as a microelectronic circuit, e.g. an application-specific development, ASIC (application-specific integrated circuit), or as a digital integrated circuit that can be configured by the customer, FPGA (field programmable gate array). One important task of the peripheral electronic detector unit could involve the control of the progress of the method over time, in other words for example using appropriate control signals to bring about the resetting of measurement values, the triggering of the emission of x-ray radiation by one of the x-ray beam sources, the storing of a measurement values in a buffer, etc. Another task could also be checking the feasibility of the method based on time parameters, such as x-ray pulse duration, time required for data transfer or the interval until a further stereoscopic image can be captured. For further processing, e.g. within the peripheral electronic detector unit or in a system computation unit, it is expedient to digitize analog measurement values, i.e. to perform an analog-to-digital conversion. A further task of the peripheral electronic detector unit can be an initial preparation of the x-ray image datasets. This could include for example simple image operations, such as cropping, rotating or scaling the datasets, or detector-specific corrections, such as the masking of image point errors or the correction of an offset from the dark current of the sensor, or the combining of image points, also referred to as binning.

At least some of the first and second x-ray image dataset is visualized with the aid of a display means embodied for stereographic representation.

A further basic concept of the application relates to a system unit for stereoscopic x-ray imaging. The system unit comprises an x-ray radiation detector, a stereoscopic x-ray tube and a peripheral electronic detector unit. The x-ray radiation detector has a scintillator, which is configured to convert x-ray beam quanta striking the x-ray radiation detector to light quanta; it also has a grid of detector units, each detector unit having a light-sensitive receiver, at which a measurement value can be changed by light quanta striking it, each detector unit also having a buffer for measurement values that can be read out from the light-sensitive receiver. The stereoscopic x-ray tube comprises two x-ray beam sources disposed a short distance from one another, the x-ray beam sources being disposed together in a housing and the x-ray beam sources being embodied so that, in an x-ray beam-emitting state, the central beams intersect in a recording plane. The components of the system unit are also configured to execute one of the methods described above.

The x-ray radiation detector allows virtually simultaneous imaging from two angles. This is important for recording images of moving organs such as the heart, aorta or liver or moving objects such as guide wires, catheters or coils. For the identical spatial assignment of a moving object in the stereo image it would be ideal if the two projection images were generated at the same time. However this is not possible in principle due to the one x-ray detector, so the task of the system unit for stereoscopic x-ray imaging is to record the two images as quickly as possible one after the other. This requires a detector technology that supports such timing. Technologies and systems used until now, for example image amplifier/TV tube camera, image amplifier/frame transfer CCD camera, CsI or a-Si-based flat screen detectors, do not allow two recordings to be generated one after the other in the shortest possible time, to document a virtually identical state of movement of the object, e.g. an organ. The application uses detectors, which are produced using CMOS technology (complementary metal oxide semiconductor) or related technologies based on crystalline silicon, and have specific properties, such as fast buffers, also referred to as shadow registers, which make it possible to carry out two separate x-ray recordings with a short interval and to perform the read-out process, which is typically relatively time-consuming, in a less time-critical phase. This approach is suitable for stereoscopic imaging involving moving objects.

It is important for the stereoscopic x-ray tube that the two x-ray beam sources are disposed a short distance from one another and can generate radiation, which is registered on the x-ray detector, one after the other. With minimum possible distances of approx. 6.5 cm to 10 cm it is to dispose the x-ray beam sources together in a housing. Alternatively for greater distances two separate emitters can also be disposed next to one another. Emitters with a grounded anode would be advantageous here as they can be designed to be smaller in structure.

In one embodiment of the application the x-ray beam sources each comprise an anode plate/cathode pair, which are disposed along a center line, and the anode plate/cathode pairs are disposed with mirror symmetry with a mirror plane perpendicular to the center line. X-ray beam sources, in which an anode plate and cathode are disposed on an center line, are known from the prior art. In this embodiment of the application it is now proposed that two such x-ray beam sources should be disposed on an center line and the geometric sequence of anode plate and cathode should be such that the position of the x-ray beam sources has mirror symmetry in respect of a perpendicular of the center line. In principle this allows sequences in which the two cathodes are disposed between the two anode plates or in which the two anode plates are disposed between the two cathodes. The latter instance has the feature that the two anode plates can be constructed closer together, with the result that the distance between the central beams of the x-ray beam sources is very short.

In a further embodiment the stereoscopic x-ray tube is embodied as a rotating envelope tube, the center line forming the axis of rotation. Rotating envelope tubes are known from the prior art. The described stereoscopic x-ray tube can be embodied with less additional outlay than a rotating envelope tube, with the center line forming the axis of rotation.

BRIEF DESCRIPTION OF THE DRAWINGS

The embodiments described in more detail below represent embodiments of the present application. Further developments will emerge from the figures and description which follow, in which.

DETAILED DESCRIPTION OF INVENTION

Figure 1:
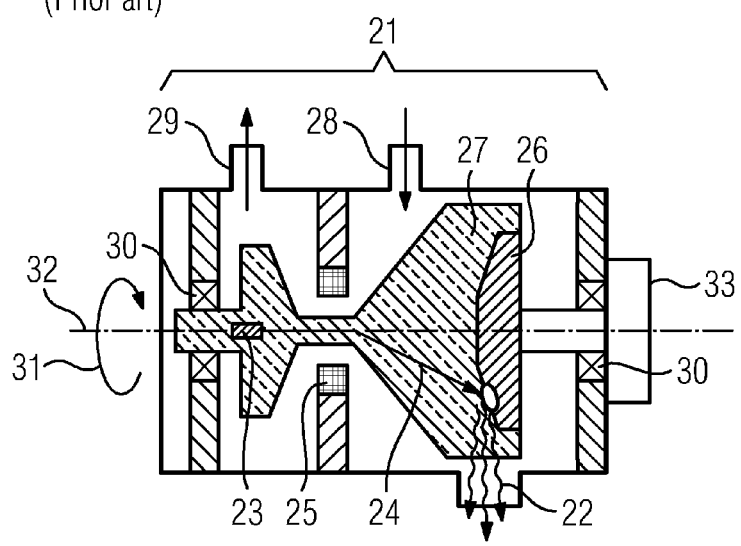
FIG. 1 shows an embodiment of an x-ray tube according to the prior art.

FIG. 1 shows an embodiment of an x-ray beam source 21, which comprises an x-ray tube for generating x-ray beams 22 according to the prior art. More specifically it comprises a cathode 23 and an anode plate 26, which are disposed in an evacuated glass body 27. The electrons 24 emitted by the cathode 23 are accelerated by a high voltage and, in some instances after their flight path has been controlled by deflection coils 25, strike the anode plate 26, where they are slowed down and generate the characteristic x-ray radiation, braking radiation and Lilienfeld radiation. The x-ray beam source 21 is embodied as a so-called rotating envelope tube. This means that the glass body 27, which is guided in bearings 30, the cathode 23 and the anode plate 26 are shaped with rotational symmetry in relation to an axis of rotation 32 and can execute a rotational movement 31 with the aid of a symbolically represented motor 33. To cool the anode plate, which becomes hot due to the electron bombardment, cooling fluid, e.g. a cooling oil, can be pumped into the apparatus via the inlet 28 and the outlet 29.

Figure 2:
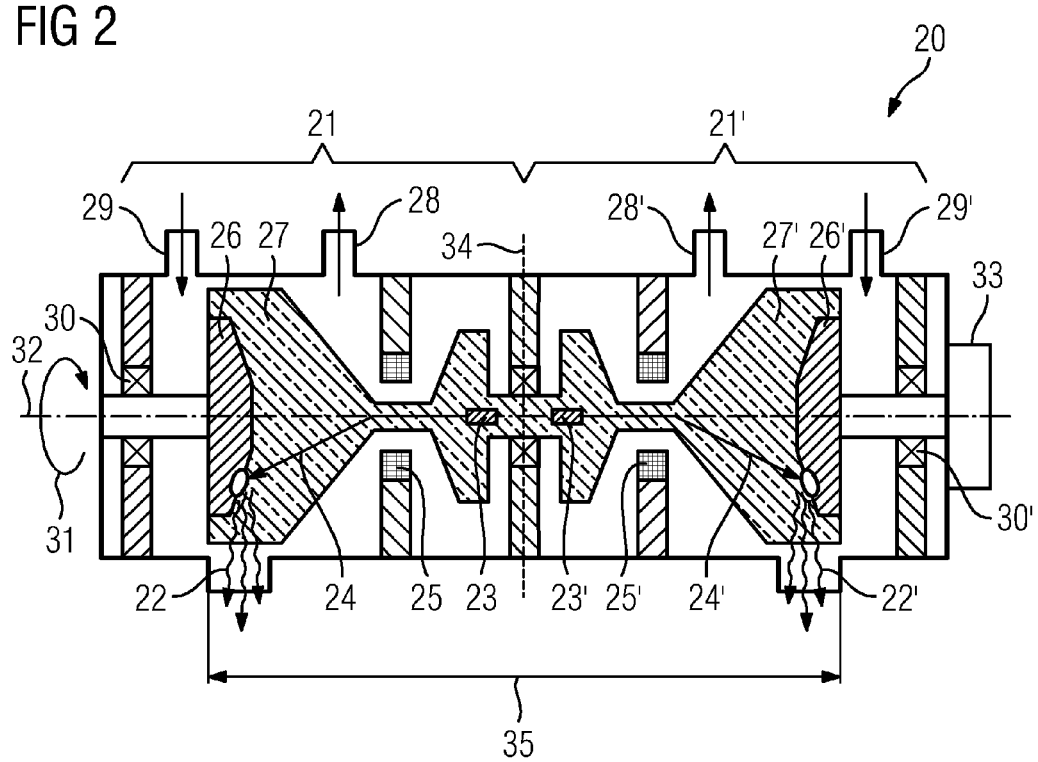
FIG. 2 shows an embodiment of a disclosed stereoscopic x-ray tube with two adjacent cathodes.

FIG. 2 shows an embodiment of a disclosed stereoscopic x-ray tube 20 with two x-ray beam sources 21 and 21' disposed at a distance 35 from one another, the so-called stereo base. The function and structure of each individual x-ray beam source 21 or 21' correspond in principle to those of the x-ray beam source 21 shown in FIG. 1, with identical reference characters designating identical components. Reference characters with an apostrophe designate the corresponding components of the second x-ray beam source 21' of the x-ray tube 20. The two x-ray beam sources 21 and 21' are disposed along the same center line 32. Furthermore the anode plate/cathode pairs 26, 23 and 26', 23' are disposed with mirror symmetry with a mirror plane 34, which is perpendicular to the center line 32. The two cathodes 23 and 23' are thus disposed in an adjacent manner between the two anode plates 26 and 26'. This arrangement allows a sufficiently short distance 35 between the two central beams 22 and 22' of the x-ray beam sources 21 and 21'. In an alternative embodiment the two glass bodies 27 and 27' are connected to one another, which has structural features, for example reduced outlay on mechanical parts, because the bearings on the mirror plane only have to be embodied once or a single vacuum is sufficient for both glass bodies 27 and 27'.

Figure 3:
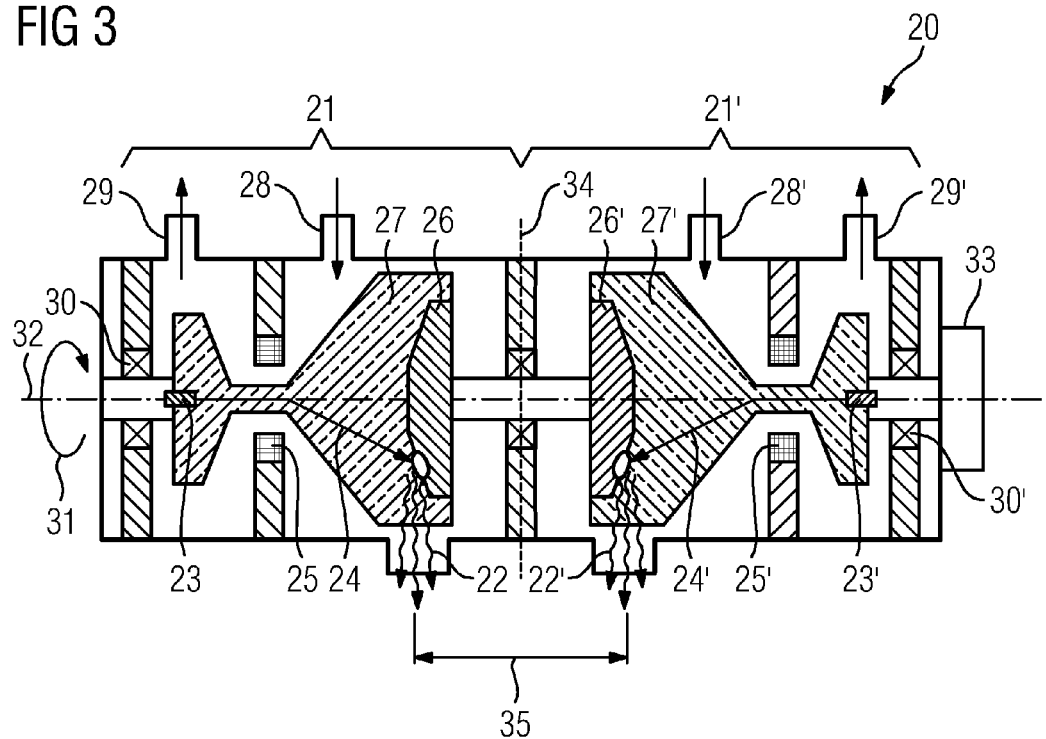
FIG. 3 shows an embodiment of a disclosed stereoscopic x-ray tube with two adjacent anode plates.

FIG. 3 shows an alternatives embodiment of the disclosed stereoscopic x-ray tube 20 with two x-ray beam sources 21 and 21' disposed at a distance 35 from one another. The function and structure of each individual x-ray beam source 21 or 21' again correspond in principle to those of the x-ray beam source 21 shown in FIG. 1, with identical reference characters again designating identical components. Reference characters with an apostrophe again designate the corresponding components of the second x-ray beam source 21' of the x-ray tube 20. The two x-ray beam sources 21 and 21' are again disposed along the same center line 32. Furthermore the anode plate/cathode pairs 26, 23 and 26', 23' are disposed with mirror symmetry with a mirror plane 34, which is perpendicular to the center line 32. In this embodiment the two anode plates 26 and 26' are disposed in an adjacent manner between the cathodes 23 and 23'. This arrangement allows an even shorter distance 35 between the two central beams 22 and 22' of the x-ray beam sources 21 and 21' than in the embodiment in FIG. 2. The two glass bodies 27 and 27' can again be connected to one another.

Figure 4:
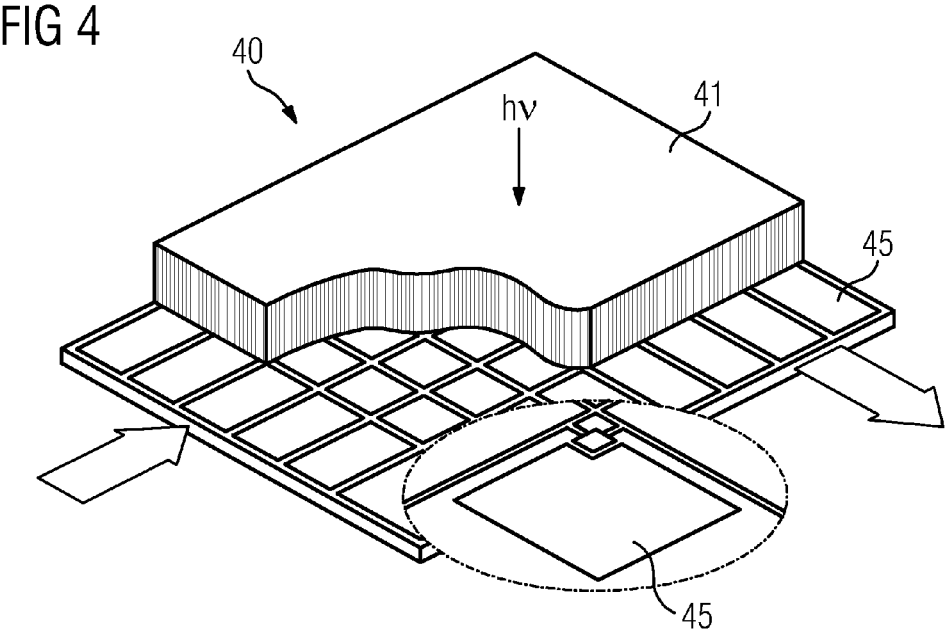
FIG. 4 shows a perspective, partly sectional representation of an x-ray radiation detector, as can be used with the application.

FIG. 4 shows a perspective, partially sectional representation of an x-ray radiation detector 40, as can be used with the application. Each x-ray radiation detector 40 consists of a plurality of x-ray radiation detector elements 45, one of which is shown enlarged in FIG. 4. The detector elements 45 have a coating of scintillator material 41, which converts x-ray beam quanta "hv" to light quanta.

Figure 5:
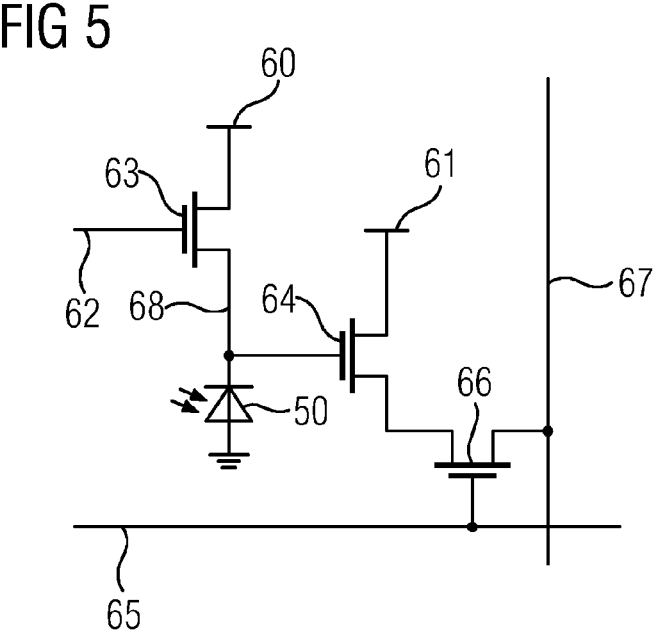
FIG. 5 shows an embodiment of a circuit of an x-ray radiation detector element, which has a light-sensitive receiver, at which a measurement value is changed by light quanta striking it.

FIG. 5 shows an embodiment of a circuit of the x-ray radiation detector element, which has a light-sensitive receiver, at which a measurement value is changed by light quanta striking it. The circuit can be produced using CMOS technology. In a first step a transistor 63 is switched to a conducting state by an appropriate switching signal 62, referred to as a reset signal, with the result that the voltage at a node 68, i.e. at the base of a transistor 64 and at the cathode of a photodiode 50, is set to a bias voltage 60. Light quanta striking the photodiode 50 cause the node at the base of the transistor 64 to discharge. After exposure the measurement values of the x-ray radiation detector elements are read out. This takes place in each instance with the aid of a transistor 66, which is selected by activating a row 65 and initiates the read-out process by way of the column 67. A transistor 64 connected in the manner of a source follower with a supply voltage 61 serves as a buffer and amplifies the voltage at the node 68, without discharging the photodiode 50 in the process. In other words the read-out is non-destructive, allowing the signal to be read out more than once for example, in order to improve noise.

Figure 6:
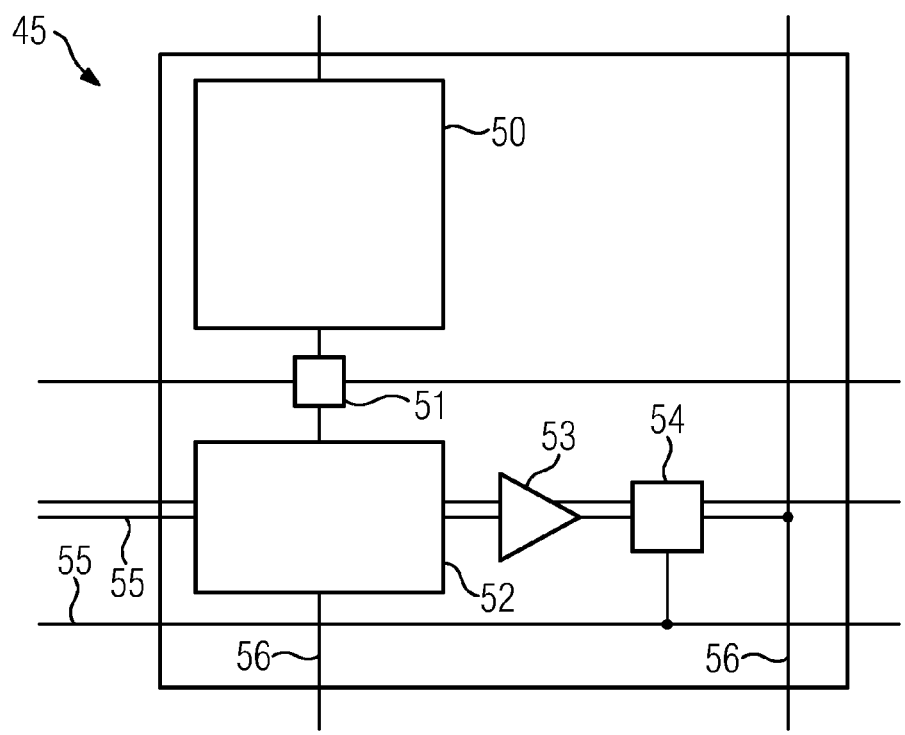
FIG. 6 shows a schematic drawing to clarify the structure of a detector element of the x-ray radiation detector used with the application.

FIG. 6 shows an example of an embodiment of the structure of an individual detector element 45. A photodiode 50 converts light quanta leaving the scintillator to an electric voltage proportional to the number of light quanta, until the voltage is reset to a specified value, that of the bias voltage. Disposed adjacent to the photodiode 50 is a so-called transfer gate 51, which has the task of forwarding the charge at the photodiode 50, in the present instance specifically to a buffer 52. Disposed downstream of the buffer 52 are an amplifier 53 and a switching transistor 54, so that the data values, i.e. the charge measurement values or voltage measurement values corresponding to said charge, can be read out from the buffer 52 into a central memory by way of read-out lines 55 in rows and read-out lines 56 in columns. In the present instance the individual detector elements 45 are to be produced using CMOS technology or related technologies.

The structure of a detector element in the manner of the detector element in FIG. 5 and FIG. 6 is known. In the present instance interest is focused on specifying an application in stereoscopic x-ray imaging with the aid of a stereoscopic x-ray tube.

Figure 7:
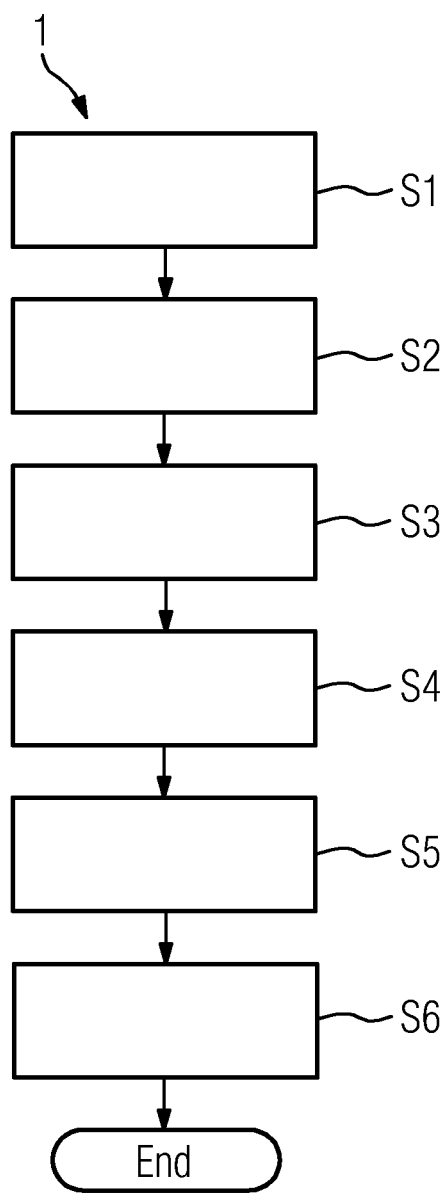
FIG. 7 shows a flow diagram of a disclosed method

FIG. 7 shows a flow diagram of a disclosed method for stereoscopic x-ray imaging with the aid of a stereoscopic x-ray tube, which comprises two x-ray beam sources disposed a short distance from one another, an x-ray radiation detector, which has a scintillator, which converts x-ray beam quanta striking the x-ray radiation detector to light quanta and which also has a grid of detector units, each detector unit having a light-sensitive receiver, at which a measurement value is changed by light quanta striking it, and each detector unit having a buffer for measurement values read out from the light-sensitive receiver. The method comprises the method steps S1 to S6 and ends "End" after method step S6. The individual method steps are as follows:

S1) Resetting the measurement values in all the light-sensitive receivers to a predefined value;

S2) Emitting x-ray radiation from the first x-ray beam source, so that said x-ray radiation passes through an image object before striking the x-ray radiation detector;

S3) Reading the measurement values out from all the light-sensitive receivers into the associated buffers and then resetting the measurement values in each receiver to the predefined value;

S4) Emitting x-ray radiation from the second x-ray beam source, so that said x-ray radiation passes through the image object before striking the x-ray radiation detector;

S5) Reading the measurement values out from all the buffers into a central memory, producing a first x-ray image dataset from the projection direction of the first x-ray beam source;

S6) Reading the measurement values out from all the light-sensitive receivers into the central memory, producing a second x-ray image dataset from the projection direction of the second x-ray beam source.

In one alternative embodiment the method is executed repeatedly with an interval until a termination criterion is satisfied.

FIG. 8 to FIG. 11 show time curves 100 to 103 for different digital signals, on the basis of which four different variants of the time sequence of the disclosed method are illustrated by way of example.

Figure 8:
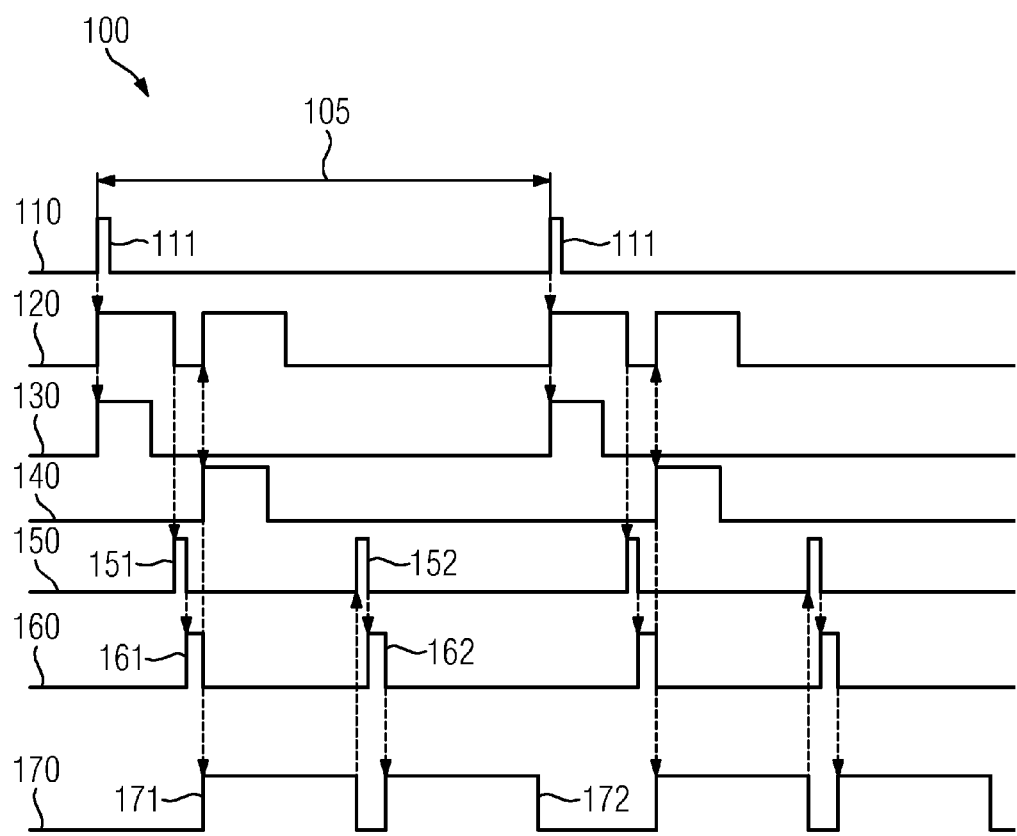
FIG. 8 to FIG. 11 show time curves for different digital variables, based on which four different variants of the disclosed method are illustrated by way of example.

The procedure according to one alternative is described first with reference to FIG. 8. In this instance there is a system trigger, which supplies pulses 111 according to the curve 110. The system trigger causes the so-called integration window of the photodiodes to be open, see pulses in curve 120. Immediately after this, according to the curve 130, x-ray radiation starts to be emitted from a first x-ray beam source. During the integration window the photodiodes measure the light quanta, with integration of the measurement values taking place in a manner known per se. After the end of the x-ray beam pulse, according to the curve 150, a data transfer pulse 151 takes place from the photodiodes into the respective buffer. The photodiodes are then reset according to the curve 160 and the pulse 161. The method now proceeds with two processes simultaneously. The data values stored in the buffers of all the detector elements are read out according to the curve 170 during a pulse 171 into a central memory. At the same time, according to the curve 120, the photodiode integration window is opened again and, according to the curve 140, x-ray radiation is now emitted from a second x-ray beam source. Once the image has been recorded, some time is spent reading out according to the curve 170. As soon as the first image has been read out from the first x-ray beam source, a data transfer according to the curve 150, pulse 152, can take place from the photodiodes into the respective buffer. As soon as the voltage values have been read from the photodiodes into the corresponding buffer, the photodiodes can be reset according to curve 160, pulse 162, and the second x-ray image can then be read out into the central memory, i.e. the 2D image dataset from the second x-ray beam source, see again the curve 170, pulse 172. The system trigger then produces a further pulse 111 and the method is repeated after a predefinable interval 105, a second stereoscopic image pair, consisting of a second image from the first x-ray beam source and a second image from the second x-ray beam source, being recorded, etc.

Figure 9:
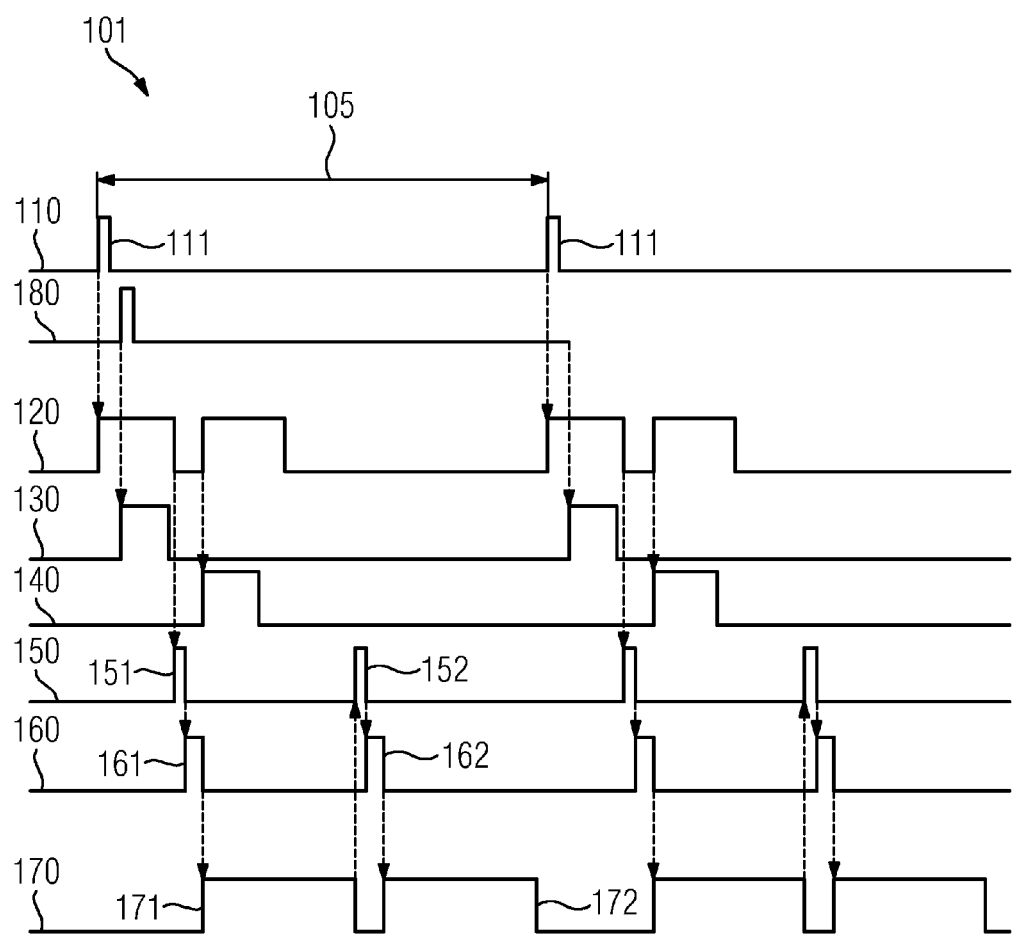

FIG. 9 shows a time curve 101 for an alternative time sequence of the disclosed method. The integration windows for a specific image frequency of the detector are generally predefined. The corresponding x-ray pulse should always be shorter than or as a maximum identical in length to the integration window, otherwise radiation would be applied, which is not of relevance to the image, which would result in unnecessary radiation exposure, for a patient for example. Generally the x-ray pulse is shorter than the integration window, the maximum length of which is known to the system even before the x-ray. If the x-ray pulse from the first x-ray beam source is now delayed so long that it occurs at the end of the detector integration window and if on the other hand the x-ray pulse from the second x-ray beam source is positioned so that it starts at the start of the second integration window, the two x-ray pulses are as a maximum close to one another in time, which has features for stereoscopic image generation, specifically the best possible "simultaneity".

Figure 10:
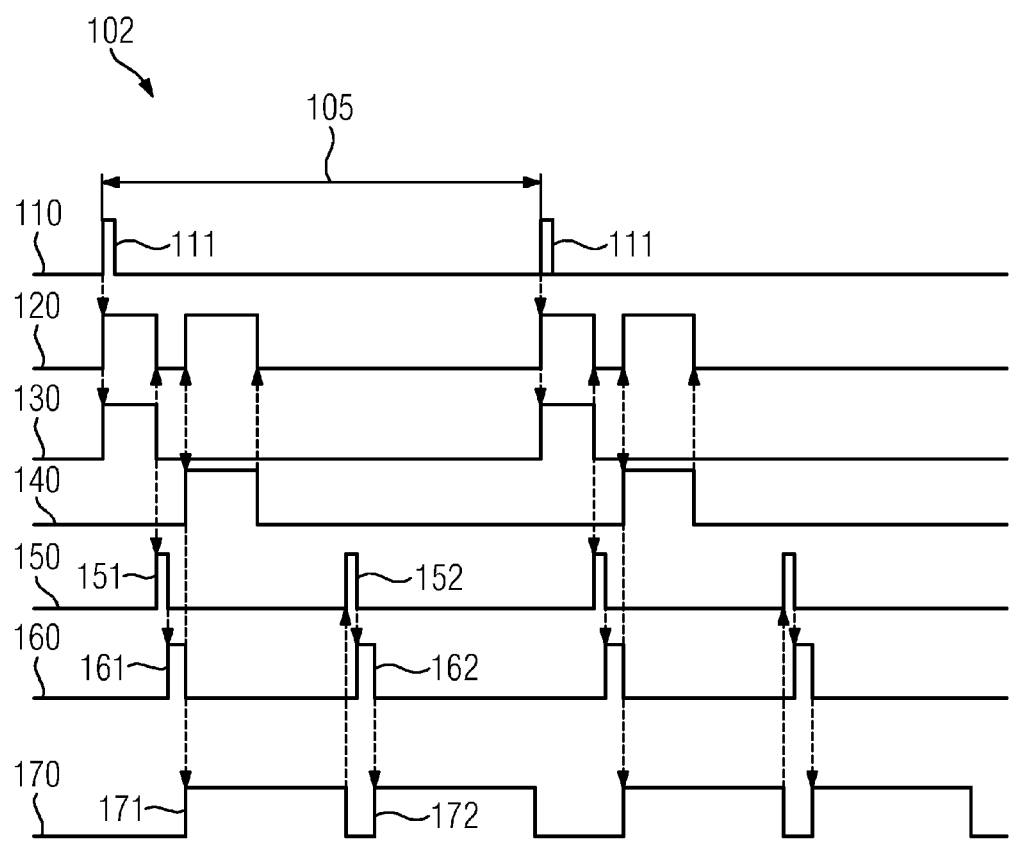

FIG. 10 shows a time curve 102 for a further alternative time sequence of the disclosed method. A timing variant is described here, with which a property of CMOS detectors is used, specifically the low level of dependence of the offset behavior or the dark current, on the integration length. If the offset changes little or not at all over a certain integration window range, e.g. 10 ms to 100 ms, or even 5 ms to 200 ms, the integration time can be set in a variable manner for offset images, which are generally produced in calibration cycles during the rest phases of x-ray imaging, i.e. when no radiation is emitted or there is no patient present in the beam path of the x-ray emitter. It can then start shortly before the start of irradiation and can end at the end of irradiation. The integration window is then always optimal, in other words minimal, and is determined by the application, such as in clinical applications, as a function of the dose, object movement, the x-ray spectrum, the anatomy of the patient, etc. Variable x-ray windows ensure that the pulses of the two x-ray beam sources remain optimally close to one another in time for all image pairs.

Figure 11:
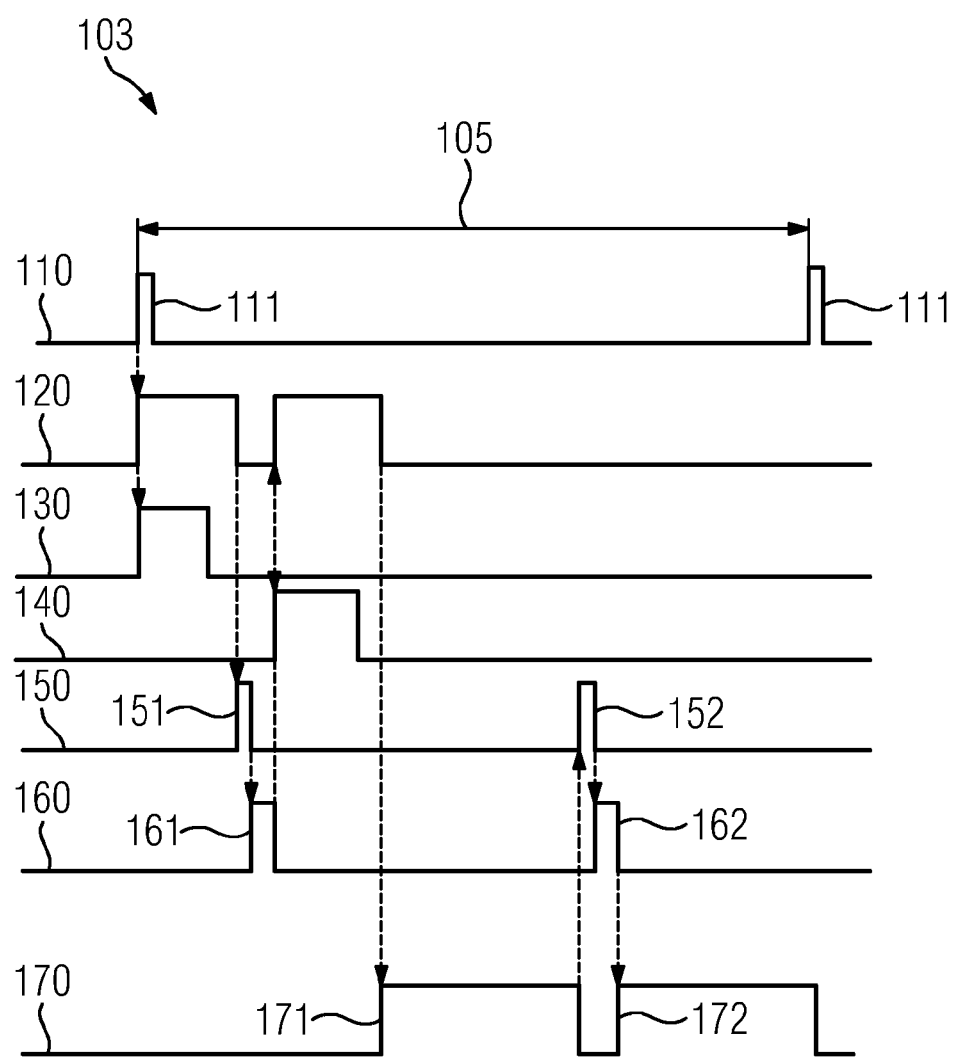

FIG. 11 shows a time curve 103 for a further alternative time sequence of the disclosed method. With this variant the buffer read-out does not take place at the same time as the acquisition of x-ray images from the second x-ray beam source, but only afterwards, see the curve 170 in FIG. 11. This extends the time period overall. However this method is possibly a more efficient way of acquiring data with as little interference as possible.

Figure 12:
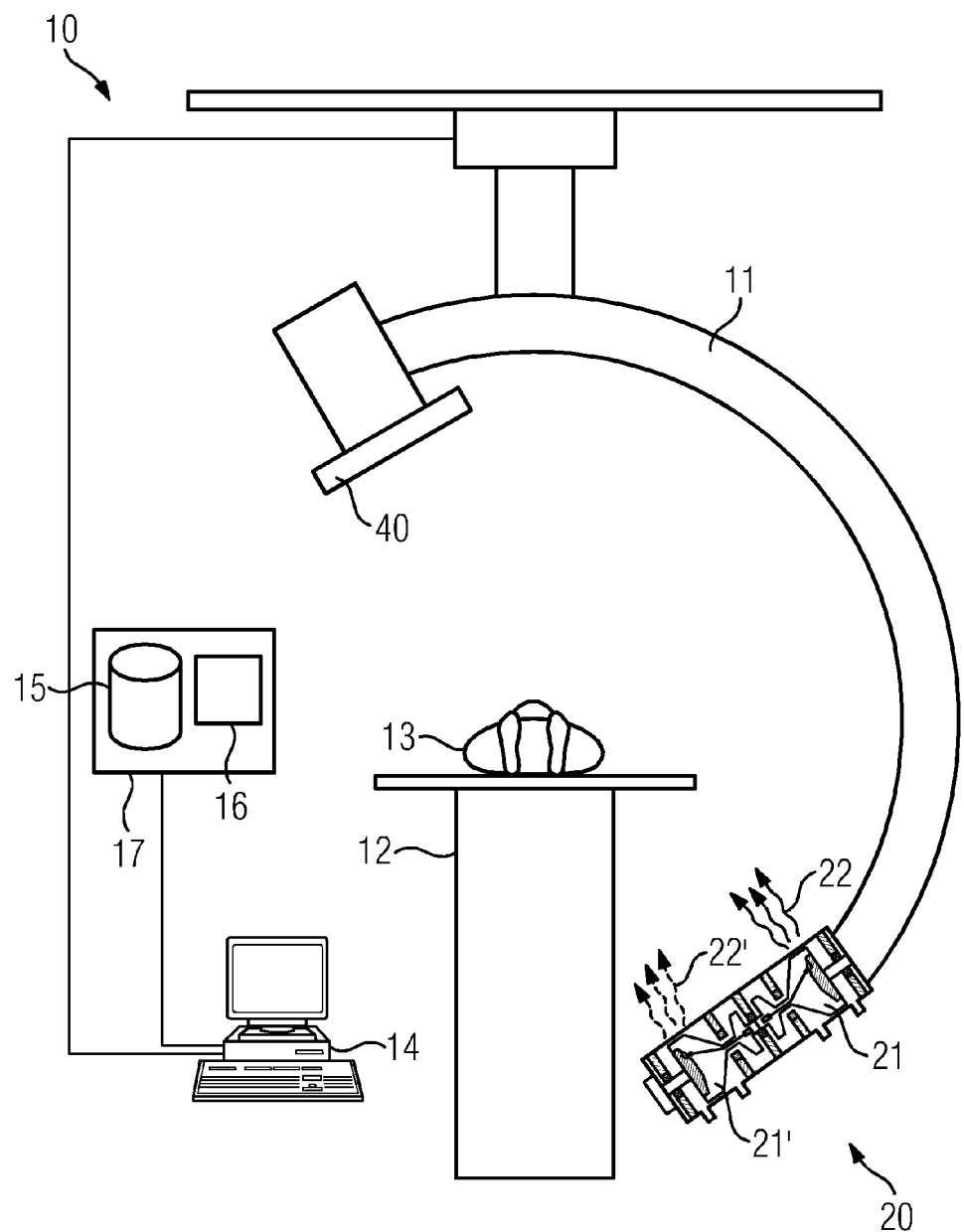
FIG. 12 shows a schematic diagram of an embodiment of a disclosed system unit for stereoscopic x-ray imaging.

FIG. 12 shows an embodiment of a system unit 10 for stereoscopic x-ray imaging. It comprises an x-ray device having a C-arm 11, on which an x-ray radiation detector 40 and a stereoscopic x-ray tube 20, which comprises two x-ray beam sources 21 and 21' disposed a short distance from one another, are disposed. The x-ray device is activated by a system computation unit 14. A patient couch 12 holding a patient 13 is positioned in such a manner that x-ray radiation 22 and 22' leaving the stereoscopic x-ray tube 20 passes through the body of the patient 13 before striking the x-ray radiation detector 40. A peripheral electronic detector unit 17 comprises a central memory 15 and an electronic circuit 16. One important task of the peripheral electronic detector unit 17 is to control the progress of a method for stereoscopic x-ray imaging and to this end also to communicate with the x-ray beam sources 21 and 21' and the x-ray radiation detector 40. During or after the acquisition of one or more stereoscopic x-ray images the peripheral electronic detector unit 17 sends the image data for example to the system computation unit 14.

Figure 13:
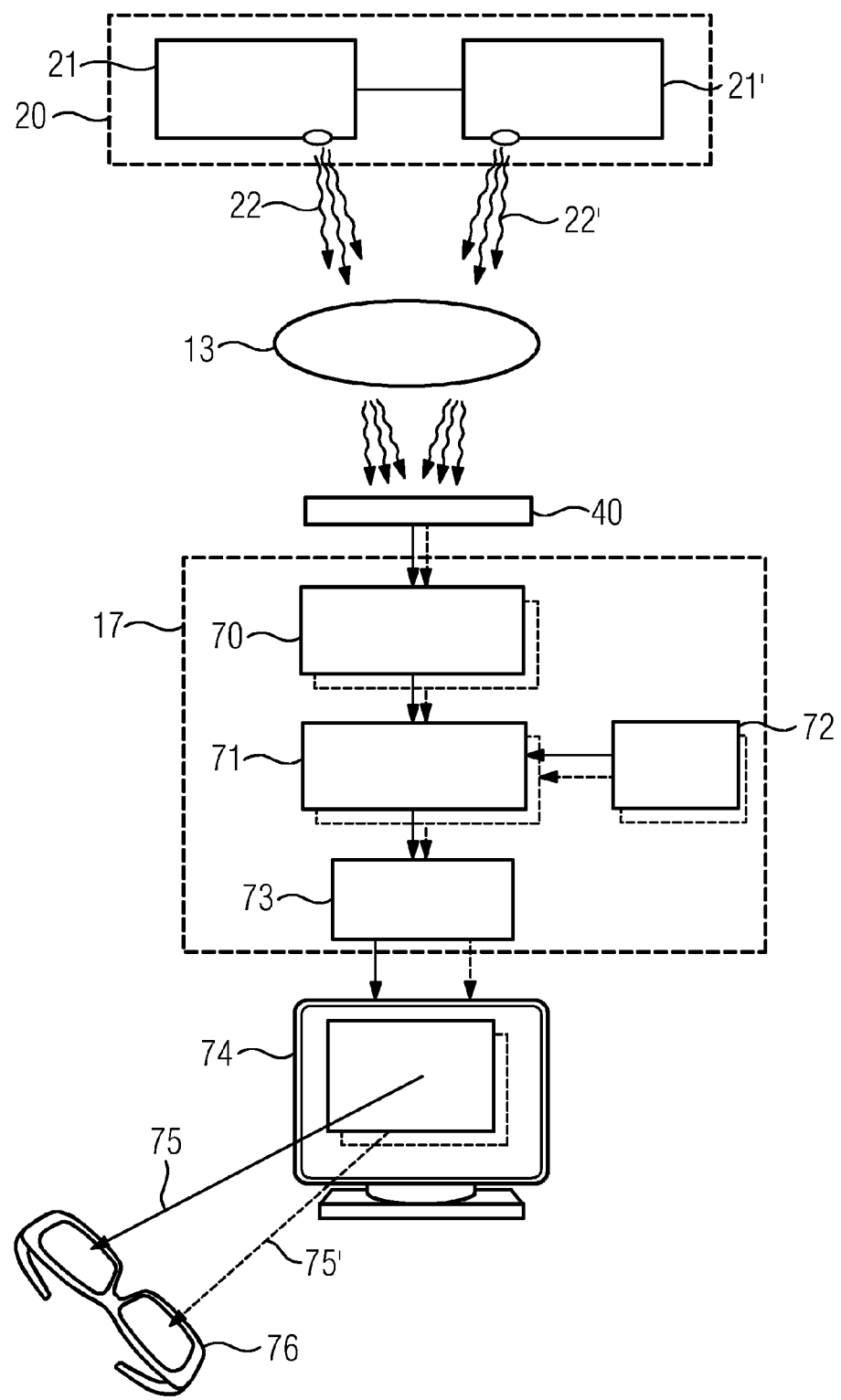
FIG. 13 shows a schematic diagram of an sequence for stereoscopic x-ray imaging.

FIG. 13 finally shows a schematic diagram of a sequence for stereoscopic x-ray imaging. Two x-ray beam sources 21 and 21' of a stereoscopic x-ray tube 20 emit two x-ray pulses 22 and 22' with a short time interval. The two x-ray beam sources 21 and 21', or their x-ray focuses, are disposed together in a housing at a short distance, e.g. 6.5 cm to 20 cm, from one another, aligned in such a manner that in an x-ray beam-emitting state the central beams intersect in a recording plane. The x-ray radiation 22 and 22' leaving the stereoscopic x-ray tube 20 passes through an examination object, e.g. the body of a patient 13, before striking an x-ray radiation detector 40. Different method steps can operate in a peripheral electronic detector unit 17: for example an analog/digital converter 70 can perform an analog to digital conversion of the detected measurement values to allow simple further processing of the measurement values, which are interpreted as image points. Or raw image data processing 71 can correct the acquired image points with the aid of calibration data 72. Or an image splitter 73 can divide up the two stereoscopic images appropriately. The two stereoscopic images are then fed to a means 74 for displaying a stereoscopic image. This means 74 can be a monitor for example, which is designed to display a stereoscopic image. A means 76 for viewing a stereoscopic image, e.g. polarizing glasses, which supplies the image acquired with the aid of the one x-ray beam source to the left eye of a viewer and the image acquired with the aid of the other x-ray beam source to the right eye of a viewer, allows a viewer to view the stereoscopic image with its impression of depth. Instead of a monitor and appropriate glasses, it is possible as an alternative to use semi-transparent stereo glasses, fitted with LED or OLED displays for example. This makes it possible to change viewing direction, for example to a catheter or patient, whilst still perceiving the stereoscopic image at the same time. In this process the information, in other words the images, from the first x-ray beam source is projected into one eye and the information, in other words the images, from the second x-ray beam source is projected into the other eye in an alternating manner.

The invention claimed is:
1. A method for stereoscopic x-ray imaging by a stereoscopic x-ray tube comprising a first and a second x-ray beam sources and by an x-ray radiation detector, comprising:
    disposing the first and the second x-ray beam sources at a distance from one another;
    converting x-ray beam quanta striking the x-ray radiation detector by a scintillator disposed on the x-ray radiation detector;

arranging a grid of detector units on the x-ray radiation detector, each detector unit having a light-sensitive receiver at which a measurement value is changed by light quanta striking the light-sensitive receiver, and each detector unit having a buffer for the measurement value read out from the light-sensitive receiver;

the method further comprising steps of:

resetting measurement values in light-sensitive receivers to a predefined value;

emitting a first x-ray radiation from the first x-ray beam source passing through an image object before striking the x-ray radiation detector;

reading the measurement values out from the light-sensitive receivers into associated buffers;

resetting the measurement values in the light-sensitive receivers to the predefined value;

emitting a second x-ray radiation from the second x-ray beam source passing through the image object before striking the x-ray radiation detector;

reading the measurement values out from the buffers into a central memory;

generating a first x-ray image dataset from a projection direction of the first x-ray beam source;

reading the measurement values out from the light-sensitive receivers into the central memory; and generating a second x-ray image dataset from a projection direction of the second x-ray beam source.

2. The method as claimed in claim 1, wherein the measurement values are read out from the light-sensitive receivers into the central memory by the buffer.

3. The method as claimed in claim 1, wherein the steps are executed repeatedly with a predefinable interval until a termination criterion is satisfied.

4. The method as claimed in claim 3, wherein the steps are terminated by an actuation of a pushbutton.

5. The method as claimed in claim 1, wherein a peripheral electronic detector unit controls progress of the steps, and/or performs an analog/digital conversion of the measurement values, and/or prepares the first and the second x-ray image datasets, and/or performs detector-specific corrections, and/or combines elements of the first and the second x-ray image datasets, and/or feeds the first and the second x-ray image datasets to a system computation unit.

6. The method as claimed in claim 5, wherein the peripheral electronic detector unit prepares the first and the second x-ray image datasets by changing a geometric arrangement.

7. The method as claimed in claim 1, wherein at least some of the first and some of the second x-ray image datasets are visualized by a display for stereographic representation.

8. A system unit for stereoscopic x-ray imaging, comprising:

a stereoscopic x-ray tube comprising a first and a second x-ray beam sources disposed at a distance from one another in a housing, wherein central beams emitted from the first and the second x-ray beam sources intersect in a recording plane;

an x-ray radiation detector comprising:

a scintillator for converting x-ray beam quanta striking the x-ray radiation detector to light quanta, and a grid of detector units, each detector unit comprising:

a light-sensitive receiver at which a measurement value is changed by light quanta striking the light-sensitive receiver, and a buffer for a measurement value that is read out from the light-sensitive receiver, and a peripheral electronic detector unit that is configured to execute method steps as claimed in claim 1.

9. The system unit as claimed in claim 8, wherein the first and the second x-ray beam sources each comprises an anode plate/cathode pair disposed along a center line, and wherein the anode plate/cathode pair is symmetrically disposed by a mirror plane perpendicular to the center line.

10. The system unit as claimed in claim 9, wherein the stereoscopic x-ray tube is a rotating envelope tube and rotates by the center line as an axis of rotation.

\* \* \* \* \*